United States Patent [19]

Ohkuwa et al.

[11] Patent Number: 4,802,460
[45] Date of Patent: Feb. 7, 1989

[54] ENDOSCOPE ILLUMINATING OPTICAL SYSTEM DEVICE

[75] Inventors: Hideki Ohkuwa; Akira Hasegawa, both of Hachioji, Japan

[73] Assignee: Olympus Optical Co., Ltd., Tokyo, Japan

[21] Appl. No.: 56,832

[22] Filed: Jun. 2, 1987

[30] Foreign Application Priority Data

Jun. 6, 1986 [JP] Japan ................... 61-131463

[51] Int. Cl.⁴ .................................. A61B 1/06
[52] U.S. Cl. ........................ 128/6; 350/96.26
[58] Field of Search ...................... 128/3, 4, 5, 6, 7; 350/96.26

[56] References Cited

U.S. PATENT DOCUMENTS

| | | | |
|---|---|---|---|
| 3,261,349 | 7/1966 | Wallace | 128/6 |
| 3,799,150 | 3/1974 | Bonnet | 128/6 |
| 4,272,156 | 6/1981 | Ishibashi et al. | 350/96.26 |
| 4,403,273 | 9/1983 | Nishiota | 128/6 X |
| 4,660,982 | 4/1987 | Okada | 128/6 X |

FOREIGN PATENT DOCUMENTS

| | | | |
|---|---|---|---|
| 136365 | 4/1985 | European Pat. Off. | 128/6 |
| 0161834 | 11/1985 | European Pat. Off. | |
| 3202080 | 10/1982 | Fed. Rep. of Germany | |
| 3216439 | 11/1983 | Fed. Rep. of Germany | |
| 59-96001 | 6/1984 | Japan | |

Primary Examiner—William H. Grieb
Attorney, Agent, or Firm—Armstrong, Nikaido Marmelstein & Kubovcik

[57] ABSTRACT

An endoscope illuminating optical system device wherein a light guide inserted through an insertable part of an endoscope and transmitting an illuminating light to an observing system is formed to be noncircular as a whole on the exit end surface at the front end and an illuminating optical member formed to be of a cross-section as a whole substantially of the same shape and size as of the exit end surface of the light guide and distributing the illuminating light projected out of the exit end surface of the light guide to an object to be observed is provided in a position opposed to the exit end surface of the light guide.

18 Claims, 6 Drawing Sheets

4,802,460

ENDOSCOPE ILLUMINATING OPTICAL SYSTEM DEVICE

FIELD OF THE INVENTION

This invention relates to an endoscope illuminating optical system device wherein are used illuminating optical parts for improving light distributing characteristics.

RELATED ART STATEMENT

Recently there has come to be extensively used an endoscope whereby the elongate insertable part can be inserted into a body or pipe cavity to observe or inspect the interior.

Now, as generally an external illuminating light does not reach the position in which the insertable part of the above mentioned endoscope is inserted, the endoscope is provided with an illuminating optical system together with an observing optical system.

In the above mentioned illuminating optical system, an illuminating light from a light source device is transmitted through a light guide inserted through the insertable part and is projected out of the tip surface of the light guide to illuminate the visual field range set by the observing optical system.

In such case, in a prior art example disclosed, for example, in the Gazette of Japanese Utility Model Laid Open No. 96001/1984, an illuminating lens substantially of the same diameter has been arranged in front of a light guide of a solid circular tip cross-section or single fibers to diffuse the illuminating light so as to cover the visual field range of the observing optical system.

There have been defects that, if the tip surface of the light guide is regulated to be circular as in the above mentioned prior art example, the cross-sectional area of the light guide will not be able to be made large in the space for the fine diameter insertable part, the illuminating light amount will be likely to be insufficient and it will be difficult to obtain an optical image of a brightness easy to observe.

In such case, if the outside diameter of the insertable part is made large, the cross-sectional area of the light guide will be able to be made also large. However, there are defects that, if the insertable part is made large in the diameter, a great pain will be undesirably forced to the patient in case it is inserted and the range of uses in which it can be inserted and used will become narrow.

OBJECTS AND SUMMARY OF THE INVENTION

An object of the present invention is to provide an endoscope illuminating optical system device whereby, without making the diameter of the insertable part large, the illuminating light amount can be increased and the visual field range can be brightly illuminated.

Another object of the present invention is to provide an endoscope illuminating optical system device whereby the distribution of the illuminating light can be efficiently expanded.

A further object of the present invention is to provide an endoscope illuminating optical system devide whereby the visual field range can be uniformly illuminated.

Another object of the present invention is to provide an endoscope illuminating optical system device whereby the loss of the illuminating light amount can be reduced.

In the present invention, the projecting end surface at the front end of a light guide inserted through the insertable part of an endoscope and transmitting an illuminating light for an observing means is formed to be noncircular as a whole and an illuminating optical member having a cross-sectional shape formed as a whole to be substantially of the same shape and size as of the projecting end surface of the above mentioned light guide and distributing the illuminating light projected out of the projecting end surface of the above mentioned light guide to an object to be observed is provided in a position opposed to the projecting end surface of the above mentioned light guide.

The other features and advantages of the present invention will become apparent enough with the following explanation.

BRIEF DESCRIPTION OF THE DRAWINGS

FIG. 1 is a cross-sectional view of an endoscope tip part.

FIG. 2 is a longitudinally sectioned view of the endoscope tip part.

FIG. 3 is a sectioned view on line A—A' in FIG. 2.

FIG. 4 is a perspective view showing a flexible endoscope.

FIG. 5 is a longitudinally sectioned view of an endoscope tip part.

FIG. 6 is a sectioned view on line B—B' in FIG. 5.

FIG. 7 is a partly sectioned elevation of the endoscope tip part.

FIG. 9 is a longitudinally sectioned view showing a tip adaptor.

FIG. 10 is an elevation of the tip adaptor.

FIG. 11 is a longitudinally sectioned view showing a tip adaptor.

FIG. 12 is an elevation of the tip adaptor.

FIG. 13 is a side view showing a tip part of a light guide.

FIG. 14 is an elevation showing single fibers.

FIG. 15 is a side view showing a tip part of a light guide.

FIG. 16 is an elevation showing single fibers.

FIG. 17 is an elevation showing a tip surface of a light guide and a lens.

FIG. 18 is a sectioned view on line C—C' in FIG. 17.

DETAILED DESCRIPTION OF THE PREFERRED EMBODIMENTS

The first embodiment of the present invention is shown in FIGS. 1 to 4.

Figure 4:
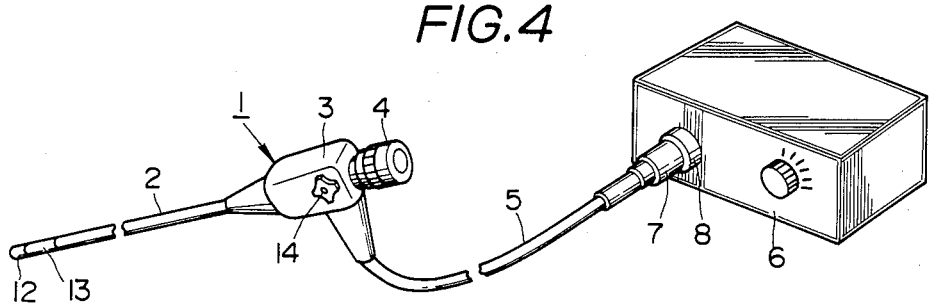

As shown in FIG. 4, a flexible endoscope 1 provided with the first embodiment is formed of an elongate flexible insertable part 2, an operating part 3 connected to the enlarged rear end of the insertable part and an eyepiece part 4 formed at the rear end of the operating part 3 and a flexible light guide cable 5 is extended out of the side of the operating part 3.

A light guide connector 7 fittable to a light source device 6 is formed at the end of the above mentioned light guide cable 5.

The above mentioned (light guide) connector 7 can be removably fitted to a connector receiver 8 of the light source device 6 so that an illuminating lamp within the light source device 6 may radiate an illuminating light onto an entrance end surface through a condenser. This radiated illuminating light is inserted through the light guide cable 5 and insertable part 2, is passed through a light guide 11 formed of a flexible fiber bundle of optical fibers and is projected out of the front end surface of the fiber bundle.

Now, a rigid tip part 12 is formed at the front end of the above mentioned insertable part 2 and the light guide 11 is secured at the front end within this tip part 12. A curvable part 13 is formed in the rear part adjacent to this tip part 12 so as to be curvable horizontally and vertically by rotating an angle knob 14 of the operating part 3.

Figure 1:
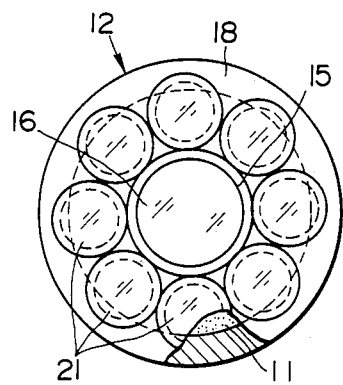
FIGS. 1 to 4 relate to the first embodiment of the present invention.
Figure 2:
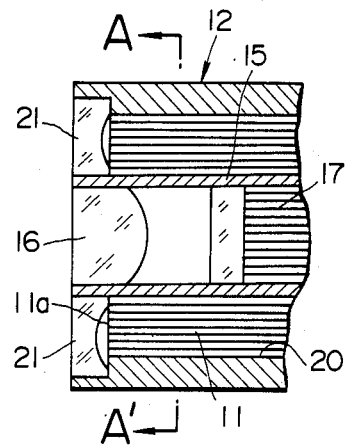
Figure 3:
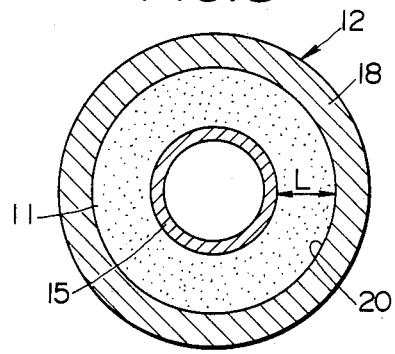

In the above mentioned tip part 12, as shown in FIGS. 1 to 3, a lens tube 15 is arranged in the center part and an objective 16 is secured within this lens tube 15 so that an optical image of an object may be formed on the front end surface of an image guide 17 by this objective 16. The optical image formed on the front end surface is transmitted to the proximal side end surface through this image guide 17 and is magnified to be observable through an eyepiece to form an observing optical system.

The light guide 11 inserted through the insertable part 2 is fitted at the front end and secured with a cement in a ring-shaped air gap part 20 between the outer periphery of the above mentioned lens tube 15 and the inner periphery of a substantially cylindrical tip member 18.

The light guide 11 is thus fitted in the ring-shaped air gap part in the outer peripheral part of the objective to increase the transmittable illuminating light amount.

In the front part of the exit end surface 11a of the front end of the above mentioned ring-shaped light guide 11, as shown in FIGS. 1 and 2, small diameter illuminating lenses 21 are fitted with a cement or the like respectively in small diameter openings on the front surface of the tip member 18 so as to fill the ring-shaped exit end surface 11a. The respective small diameter illuminating lenses 21 are formed of concave lenses of an outside diameter somewhat larger than the width L (See FIG. 3) of the ring-shaped air gap part 20 filled with the light guide 11 so as to expand and project the illuminating light projected out of the light guide exit end 11a opposed to the inside surfaces of the respective illuminating lenses 21. Many of these expanding illuminating lenses 21 are arranged in the outer peripheral part of the objective 16 so as to surround it to form an illuminating optical means illuminating the object side in the range in which the image is formed by the objective 16.

The angle of expanding the illuminating light with the above mentioned respective illuminating lenses 21 is made equal to or somewhat larger than the visual field angle of the objective 16 so that the visual field range may be illuminated brightly and substantially uniformly.

That is to say, in case one or two circular illuminating lenses in the prior art example are arranged adjacently to the objective, if the arranging positions are two shown, for example, in the cross-section in FIG. 2, a light distributing characteristic (which can substantially uniformly illuminate the visual field range) similar to that of the first embodiment will be obtained in the vertical visual field angle direction but will not be able to cover the visual field range in the horizontal direction, whereas, in the first embodiment, the same light distributing characteristic is obtained in both horizontal and vertical directions. The same light distributing characteristic is obtained not only in the horizontal and vertical directions but also in the oblique direction. That is to say, according to the first embodiment, a favorable light distributing characteristic can be realized irrespective of the direction. Further, the light guide 11 can be more effectively arranged in the space and can be made larger in the cross-sectional area and the illuminating light amount can be made sufficiently large than in the prior art example.

Figure 5:
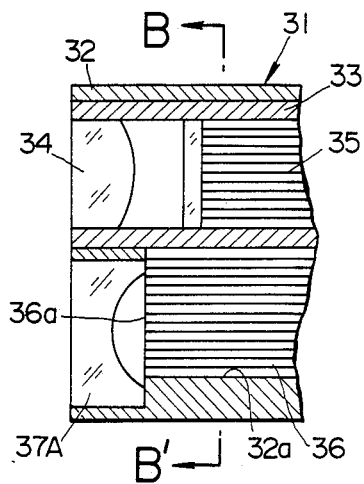
FIGS. 5 to 7 relate to the second embodiment of the present invention.

FIG. 5 shows the tip side of an insertable part in which the main part of the second embodiment of the present invention is formed.

In this part 31, a through hole is provided on the upper side of a tip member 32 to containing a lens tube 33 in which an objective 34 and an image guide 35 at the front end are secured.

Figure 6:
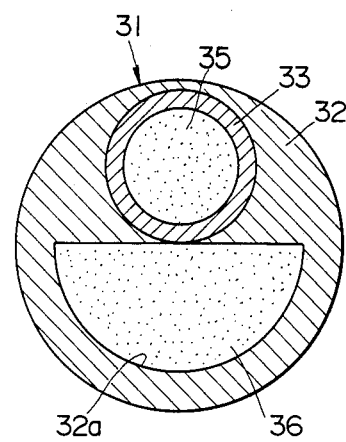

On the lower side of the above mentioned tip member 32, as shown in FIG. 6, a semicircular through hole 32a is provided on the rear side except the front end part so as to be filled with a light guide 36 secured with a cement.

Figure 7:
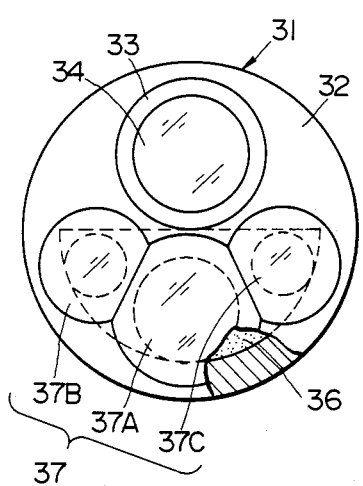

In the front surface part of the tip member 32 in the front part of the exit end surface 36a at the front end of the light guide 36 fitted in the above mentioned semicircular through hole 32a, an illuminating lens 37 integrating three circular concave lenses 37A, 37B and 37C is fitted as shown in FIG. 7.

In the above mentioned integrated illuminating lens 37, the concave lens 37A of a rather large diameter in the middle is linearly incised in the oblique upper parts on both sides and the concave lenses 37B and 37C of a rather small diameter having corresponding linear incisions are cemented to these incisions of the concave lens 37A. This integrated illuminating lens 37 is of a semicircular or meniscus shape substantially covering the semicircular front end surface of the light guide 36.

In this second embodiment, too, the light guide 36 is made large in the cross-sectional area to increase the transmittable illuminating light amount. By the illuminating lens 37 integrated by cementing the circular lenses, the light distributing characteristic is improved to be higher than in the case of using a single lens as divided into two parts. That is to say, in case two semicircular concave lenses into which a single lens of a large diameter is divided are used, the light amount distributed to the upper side on which the objective 34 is provided will be reduced, whereas, with the illuminating lens 37 forming the second embodiment, the light can be sufficiently distributed even to the upper side.

Figure 8:
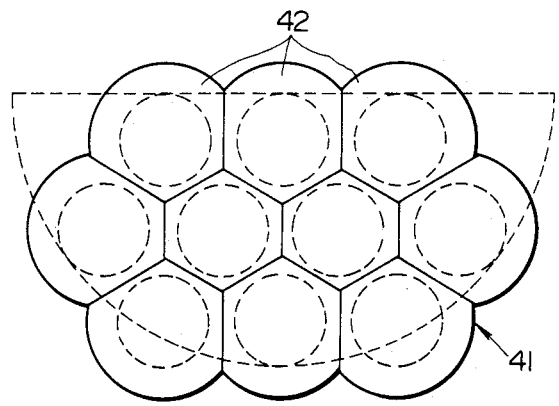
FIG. 8 is an elevation showing illuminating lenses in the third embodiment of the present invention.
Figure 10:
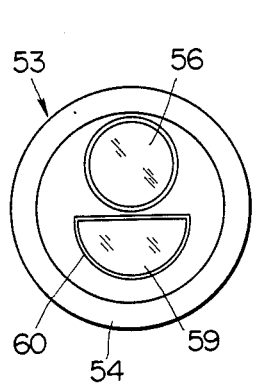
FIGS. 9 and 10 relate to the fourth embodiment of the present invention.

By the way, an illuminating lens 41 in the third embodiment shown in FIG. 8 can be also used instead of the illuminating lens 37 shown in FIG. 7.

This illuminating lens 41 is formed by cementing many concave lenses 41 which are linearly incised on the adjacent sides so as to be truly hexagonal on the sides.

Figure 9:
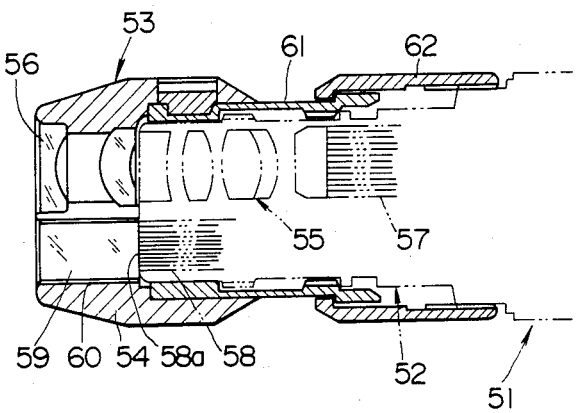

FIG. 9 shows an endoscope tip adaptor provided with the fourth embodiment of the present invention.

A tip adaptor 53 can be fitted by screwing to the tip part 52 of an endoscope 51.

In an adaptor body 54 forming this tip adaptor 53, a view angle varying lens 56 for narrow angles is fitted in a through hole provided in a position opposed to an objective 55 of the endoscope 51. An optical image of an object is formed on the tip surface of an image guide 57.

On the other hand, in the adaptor body 54 part opposed to the exit end surface 58a of a light guide 58 secured at the front end to the endoscope tip part 52, the semicircular single fiber bundle (or optical rod) 59 (solid in the cross-section) substantially equal to the shape of the exit end surface 58a of this light guide 58, that is, a semicircular shape is fitted.

As this embodiment is for observing narrow angles, the visual field range can be illuminated through the single fiber bundle 59. By the way, the single fiber bundle 59 is secured on the outer peripheral surface with a cement 60 of a low refractive index in the through hole of the adaptor body 54 so that the illuminating light may be reflected in the boundary with this low refractive index cement layer to prevent the light amount loss on the side surface of the single fiber bundle 59.

By the way, the adaptor body 54 is connected with a connecting ring 62 screwable to the tip part 52 through a cylindrical connecting member 61.

Figure 11:
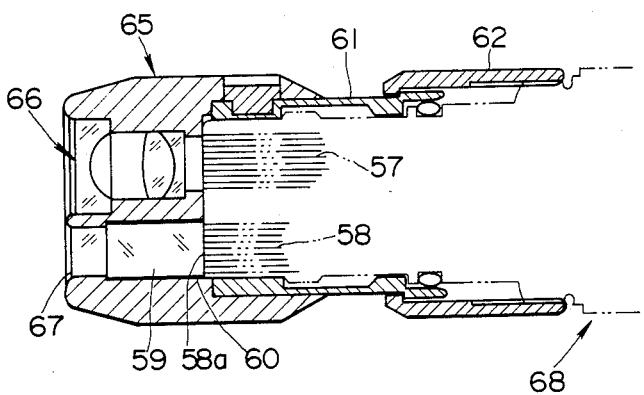
Figure 14:
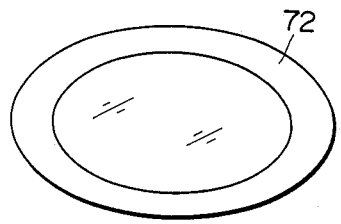
FIGS. 13 and 14 relate to the sixth embodiment of the present invention.

FIG. 11 shows a tip adaptor 65 provided with the fifth embodiment of the present invention.

Figure 12:
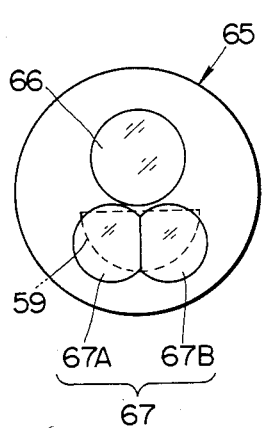
FIGS. 11 and 12 relate to the fifth embodiment of the present invention.

In the tip adaptor 65 relating to this fifth embodiment, there is fitted an objective 66 for a wide angle instead of the narrow angle in the tip adaptor 53 of the above mentioned fourth embodiment. Also, in this tip adaptor 65, an illuminating lens 67 expanding to be of a wide angle is fitted to the front of the semi-circular single fiber bundle 59. This illuminating lens 67 is made to be of a shape matching the semi-circular shape of the single fiber bundle 59 by integrating, for example, two convex lenses 67A and 67B as shown in FIG. 12 by incising them in parts of the outer peripheries adjacent to each other so as to show a light distributing characteristic of expanding in a wide angle the illuminating light projected out of the front surface of the single fiber bundle 59.

By the way, in an endoscope 68 to which this tip adaptor 65 is fitted, an image is formed directly in the image guide 57 by the above mentioned objective. That is to say, in this endoscope 68, the tip adaptor 65 is used as always fitted. In such case, the tip adaptor for a narrow angle shown in FIG. 9 can be also used as fitted. By the way, this tip adaptor 65 may be used as fitted to the endoscope shown in FIG. 9.

Figure 13:
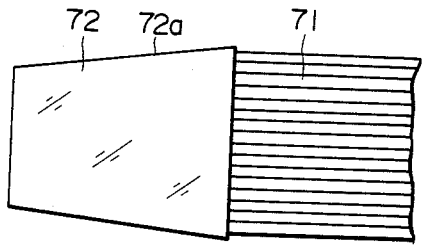
Figure 16:
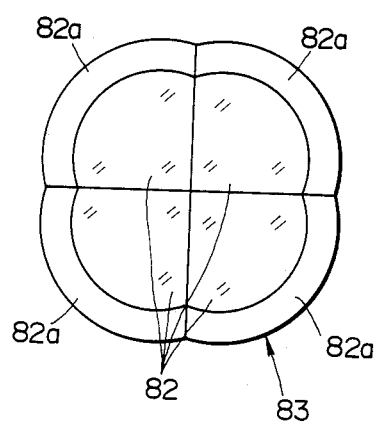
FIGS. 15 and 16 relate to the seventh embodiment of the present invention.

FIG. 13 shows the sixth embodiment of the present invention.

In this sixth embodiment, a light guide 71 not circular but modified (for example, elliptic) in the cross-section is used for the illumination and a single fiber bundle 72 formed to be of a tapered surface 72a thin on the front end side and thick on the rear end side (light guide 71 side) is arranged as an illuminating optical part for a wide angle on the exit end surface 71a of this light guide 71.

The illuminating light projected out of the front end surface of the above mentioned light guide 71 is reflected by the tapered surface 72a of the single fiber bundle 72 so as to be projected as expanded. Therefore, the illuminating lens is unnecessary. By the way, a clad layer of a low refractive index may be formed on the tapered surface 72a.

Figure 15:
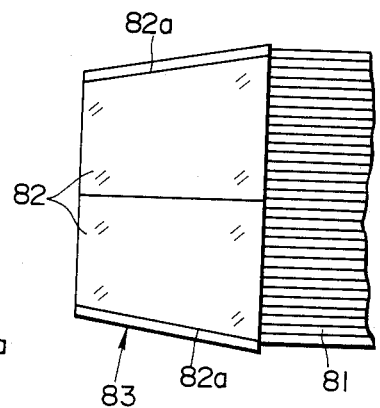

FIG. 15 shows the seventh embodiment of the present invention.

In this seventh embodiment, an optical part 83 made by cementing four single fiber bundles 82 having tapered surfaces 82a thinner on the front end side the same as in the sixth embodiment is arranged on the front surface of a light guide 81 of a cross-sectional shape different from that of the sixth embodiment.

The function and effect of this seventh embodiment are substantially the same as those of the above mentioned sixth embodiment.

Figure 17:
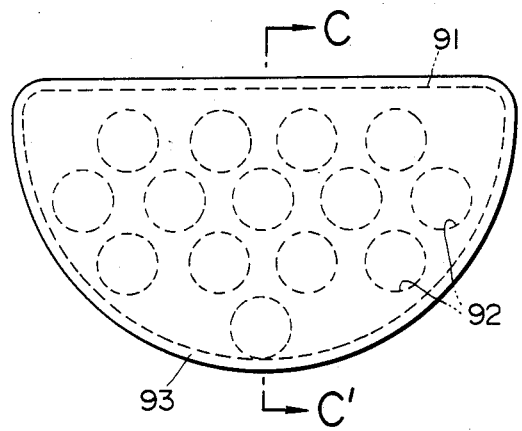
FIGS. 17 and 18 relate to the eighth embodiment of the present invention.
Figure 18:
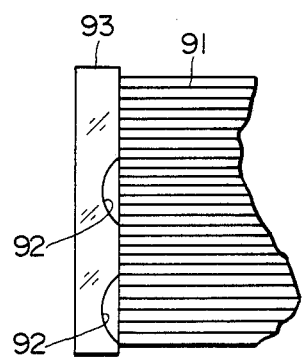

FIG. 17 shows the eighth embodiment of the present invention.

A lens 93 of a plurality of spherical recesses provided with a plurality of concaves 92 on the surface of one half of a transparent disc is provided on the front surface of a light guide 91 semicircular in the cross-section.

According to this embodiment, it is easy to produce and assemble the lens 93 to be used for illumination.

Figure 19:
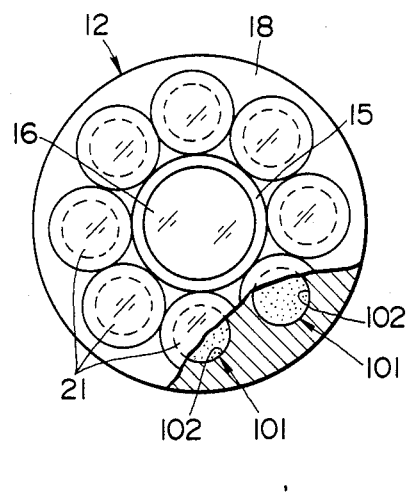
FIG. 19 is a partly sectioned elevation of an endoscope tip part in the ninth embodiment of the present invention.

FIG. 19 shows the ninth embodiment of the present invention.

In this embodiment, the light guide 11 inserted in the form of a ring concentric with the image guide 17 through the insertable part is divided on the front end side into many circular fiber bundle parts 101. For example, in the tip member 18, many circular through holes 102 are provided around a through hole in which the lens tube 15 is fitted and the above mentioned fiber bundle parts 101 are fitted in the respective through holes 102 and are secured with a cement or the like. The respective through holes 102 are expanded in the diameter on the front end side so as to be stepped.

According to this ninth embodiment, all the illuminating light can be positively projected out of the exit end surface at the front end of the light guide 11 so that the loss of the illuminating light amount may be reduced to be less than in the first embodiment. As the light is not intercepted, the temperature of the tip part can be prevented from rising due to the light intercepting part.

Figure 20:
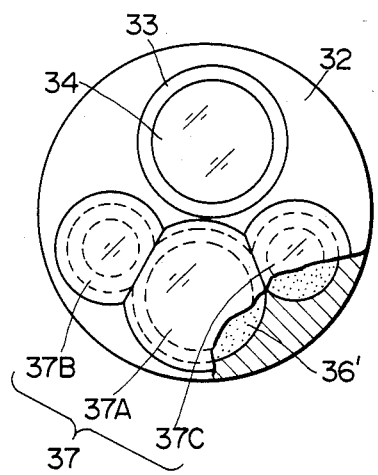
FIG. 20 is a partly sectioned elevation of an endoscope tip part in the tenth embodiment of the present invention.

FIG. 20 shows the tenth embodiment of the present invention.

In this embodiment, the semicircular light guide 36 shown in FIG. 6 is made a light guide 36' of a shape conforming to the contour of the illuminating lens 37 just in front of the end surface. Its function and effect are the same as those of the above mentioned ninth embodiment.

Figure 21:
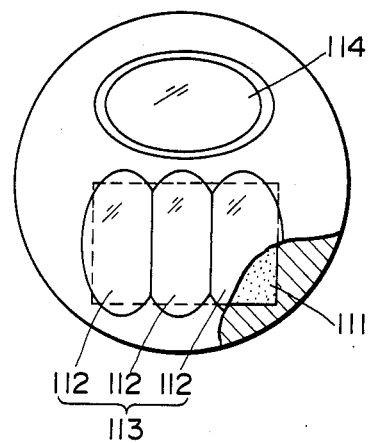
FIG. 21 is a partly sectioned elevation of an endoscope tip part in the eleventh embodiment of the present invention.

FIG. 21 shows the eleventh embodiment of the present invention.

In this embodiment, an illuminating lens 113 made of elliptic concave lenses 112 arranged and cemented with each other in the short diameter direction is provided on the exit surface at the front end of a light guide 111 rectangular in the cross-section. An objective 114 rectangular in the conture with the long axis in the horizontal direction is provided above this lens 113.

The above mentioned objective 114 is made by grinding or otherwise working a circular form to be an elliptic form. The front end surface of an image guide elliptic in the cross-section (not illustrated) is to face the focal plane of this objective 11. The above mentioned objective 114 may be circular but may be elliptic so that the useless part in an ordinary rectangular television picture surface may be reduced in the display. Also, even in case such solid state imaging device as a CCD is used and the imaging surface of this device is rectangular, this embodiment can be utilized.

Figure 22:
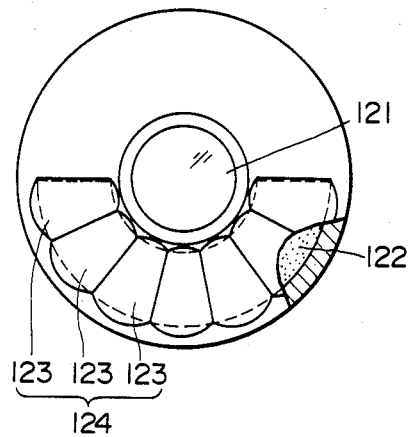
FIG. 22 is a partly sectioned elevation of an endoscope tip part in the twelfth embodiment of the present invention.

FIG. 22 shows the twelfth embodiment of the present invention.

In this embodiment, a band-shaped light guide 122 is arranged substantially in the form of a fan so as to enclose half the outer periphery of a central objective 121 around this objective 121 and a substantially fan-shaped illuminating lens 124 made by cementing substantially elliptic concave lenses 123 along the semicircular exit end surface of the light guide 122 in the short diameter direction is arranged just in front of the front end surface of the band-shaped light guide 122.

By the way, in the present invention, further another embodiment can be formed by combining or modifying the above described embodiments.

As described above, according to the present invention, as the cross-sectional area of the light guide can be made large and the optical member distributing the illuminating light is arranged in the form corresponding to the shape of the exit end surface at the front end of the light guide, the observable visual field range can be efficiently and brightly illuminated with the observing optical system.

It is apparent that, in this invention, working modes different in a wide range can be formed on the basis of this invention without departing from the spirit and scope of the invention. This invention is not restricted by its specific working mode except being limited by the appended claims.

What is claimed is:

1. An endoscope illuminating optical system device comprising:
   a light guide inserted through an insertable part of an endoscope said light guide having an exit end surface and transmitting an illuminating light to an observing means; and
   an illuminating optical member arranged in a position opposed to the exit end surface of said light guide, said illuminating optical member having a plurality of lens parts arranged so that the cross-section of said lens parts taken as a whole is substantially of the same shape and size as the cross-section of the exit end surface of said light guide and distributing the illuminating light projected out of the exit end surface of said light guide to an object to be observed.

2. An endoscope illuminating optical system device according to claim 1 wherein said illuminating optical member is formed by integrating said plurality of lens parts to provide a wide angle lens substantially of the same shape and size as the shape and size of the exit end surface of said light guide.

3. An endoscope illuminating optical system device according to claim 1 wherein said light guide has the exit end surface arranged in the form of a ring on the outer periphery of an objective of the observing means and said illuminating optical member is formed by arranging in the form of a ring a plurality of illuminating lenses of a diameter substantially equal to the width of the ring of the exit end surface of said light guide so as to cover the exit end surface of said light guide.

4. An endoscope illuminating optical system device according to claim 1 wherein said light guide is formed to be semicircular on the exit end surface and said illuminating optical member is formed of a central illuminating lens having a diameter substantially equal to the radius of the semicircle of the exit end surface of said light guide and two illuminating lenses provided on both sides of this central illuminating lens and smaller in the diameter than said central lens so as to be substantially semicircular in the entire cross-section.

5. An endoscope illuminating optical system device according to claim 4 wherein said illuminating optical member has said central illuminating lens and said two illuminating lenses of a smaller diameter linearly incised in the parts adjacent to each other and cemented with each other in these incised parts.

6. An endoscope illuminating optical system device according to claim 1 wherein said light guide is formed to be semicircular on the exit end surface and said illuminating optical member is formed by cementing many illuminating lenses so as to be substantially semicircular in the entire cross-section.

7. An endoscope illuminating optical system device according to claim 6 wherein said many illuminating lenses are linearly incised in the parts adjacent to each other and are cemented with each other in these incised parts.

8. An endoscope illuminating optical system device according to claim 1 wherein said light guide is formed to be semicircular on the exit end surface and said illuminating optical member is a single fiber bundle or optical rod semicircular in the cross-section.

9. An endoscope illuminating optical system device according to claim 8 wherein said single fiber bundle or optical rod is fixed on the outer peripheral surface with a cement low in the refractive index.

10. An endoscope illuminating optical system device according to claim 1 wherein the exit end surface of said light guide is formed to be semicircular and said illuminating optical member is comprised of an optical element having one end surface opposed to the exit end surface of said light guide and a semicircular cross-section and two illuminating lenses, each of said illuminating lenses having a linearly incised surface cemented to a linearly incised surface of the other illustrating lens with said illuminating lenses arranged to cover the other end surface of said optical element.

11. An endoscope illuminating optical system device according to claim 10 wherein said optical element is an optical rod.

12. An endoscope illuminating optical system device according to claim 1 wherein said illuminating optical member is a single fiber bundle or optical rod formed on the rear end surface to be substantially of the same shape and size as of the noncircular exit end of the light guide and to be tapered on the side surface so as to be thin on the front end side and thick on the rear end side.

13. An endoscope illuminating optical system device according to claim 1 wherein said illuminating optical member is formed by cementing four single fiber bundles or optical rods tapered on the sides so as to be thin on the front end side and thick on the rear end side and to be as a whole on the rear end surface substantially of the same shape and size as of the noncircular exit end of the light guide.

14. An endoscope illuminating optical system device according to claim 1 wherein said light guide is formed to be semicircular on the exit end surface and said illuminating optical member is formed to be semicircular in the cross-section and is provided with a plurality of concaves on at least one surface.

15. An endoscope illuminating optical system device according to claim 1 wherein said light guide is formed on the exit end surface by arranging in the form of a ring a plurality of circular end surface parts on the outer periphery of the objective of the observing means and said illuminating optical member is formed of a plurality of illuminating lenses arranged as opposed to a plurality of circular exit end surfaces of said light guide.

16. An endoscope illuminating optical system device according to claim 1 wherein said light guide is formed on the exit end surface of a central circular end surface part and two circular end surface parts provided on both sides of said central circular end surface part and smaller in the diameter than said central circular end surface part and said illuminating optical member is formed of three illuminating lenses arranged as opposed to the respective circular end surface parts of said light guide and substantially the same in the diameter as the respective circular end surface parts.

17. An endoscope illuminating optical system device according to claim 1 wherein said light guide is formed to be rectangular on the exit end surface and said illuminating optical member is formed by arranging a plurality of elliptic illuminating lenses in the short diameter direction so as to be substantially rectangular in the entire cross-section.

18. An endoscope illuminating optical system device according to claim 1 wherein said light guide is arranged on the exit end surface to be substantially fan-shaped so as to enclose half the outer periphery of the objective of the observing means and said illuminating optical member is formed by arranging a plurality of substantially elliptic illuminating lenses along the outer periphery of said objective in the short diameter direction so as to be substantially fan-shaped in the entire cross-section to cover the exit end surface of said light guide.

* * * * *